US010643321B1

United States Patent
Wang et al.

(10) Patent No.: US 10,643,321 B1
(45) Date of Patent: May 5, 2020

(54) CHARACTERIZATION METHOD FOR FINE-GRAINED SEDIMENTARY ROCK LAMINAR TEXTURE

(71) Applicant: CHINA UNIVERSITY OF PETROLEUM (EAST CHINA), Qingdao (CN)

(72) Inventors: Guanmin Wang, Qingdao (CN); Zhouhai Xiong, Qingdao (CN); Mingpeng Li, Qingdao (CN); Lingxiao He, Qingdao (CN)

(73) Assignee: CHINA UNIVERSITY OF PETROLEUM (EAST CHINA), Shandong (CN)

( * ) Notice: Subject to any disclaimer, the term of this patent is extended or adjusted under 35 U.S.C. 154(b) by 0 days.

(21) Appl. No.: 16/729,260

(22) Filed: Dec. 27, 2019

Related U.S. Application Data

(63) Continuation-in-part of application No. PCT/CN2019/084171, filed on Apr. 25, 2019.

(30) Foreign Application Priority Data

Jul. 23, 2018 (CN) .......................... 2018 1 0813521

(51) Int. Cl.
*G06T 7/00* (2017.01)
*G06T 7/73* (2017.01)
(Continued)

(52) U.S. Cl.
CPC .......... *G06T 7/0002* (2013.01); *G01N 33/24* (2013.01); *G06F 17/18* (2013.01); *G06T 5/30* (2013.01);
(Continued)

(58) Field of Classification Search
CPC .......... G06T 7/0002–0004; G06T 7/73; G06T 7/0012; G06T 7/33; G06T 7/62;
(Continued)

(56) References Cited

U.S. PATENT DOCUMENTS

| 7,020,307 | B2 * | 3/2006 | Hinton | ...................... G06T 7/62 |
| | | | | 382/109 |
| 8,492,156 | B2 * | 7/2013 | Marcelpoil | .............. G01N 1/30 |
| | | | | 436/63 |

(Continued)

FOREIGN PATENT DOCUMENTS

| CN | 105572757 A | 5/2016 |
| CN | 105954492 A | 9/2016 |

(Continued)

OTHER PUBLICATIONS

The International Search Report of corresponding International application No. PCT/CN2019/084171, dated Aug. 5, 2019.

*Primary Examiner* — Michael S Osinski
(74) *Attorney, Agent, or Firm* — J.C. Patents

(57) ABSTRACT

The present application relates to a characterization method for fine-grained sedimentary rock laminar texture, including S1: image preprocessing; S2: loading the image, and normalizing the image to a specified size; S3: performing mean filtering, dilation operation and binarization processing on the image; S4: determining whether laminars are developed; S5: determining the number of bright laminars and dark laminars; S6: determining the continuity of bright laminars and dark laminars; S7: according to the statistical result and the calculation result, recording the characterized parameters into Excel. The present application can accurately characterize the texture features of fine-grained sedimentary rock laminar. Compared with the prior art, the present application have higher efficiency and satisfies the requirement of symmetrically depicting the growth features of (Continued)

fine-grained sedimentary rock laminar, and a technical support is provided for the exploration and development of shale oil and gas.

8 Claims, 12 Drawing Sheets

(51) Int. Cl.
*G06T 5/30* (2006.01)
*G01N 33/24* (2006.01)
*G06F 17/18* (2006.01)

(52) U.S. Cl.
CPC ...... *G06T 7/73* (2017.01); *G06T 2207/10056* (2013.01); *G06T 2207/30242* (2013.01)

(58) Field of Classification Search
CPC .............. G06T 5/30; G06T 5/001–005; G06T 2207/30024; G06T 2207/10056; G06T 2207/20104; G06T 11/001; G06T 7/0016; G06T 7/136; G06T 7/155; G06T 7/174; G06T 7/48; G06T 7/90; G01N 33/24; G01N 15/1475; G06F 17/18; G06K 9/0014; G06K 9/00147; G06K 9/46; G06K 9/4671; G06K 9/00127; G06K 9/00134; G06K 9/4604
See application file for complete search history.

(56) References Cited

U.S. PATENT DOCUMENTS

| | | | |
|---|---|---|---|
| 2003/0156739 A1* | 8/2003 | Hinton | G06T 7/0004 382/109 |
| 2008/0144932 A1* | 6/2008 | Chien | G06K 9/4671 382/169 |
| 2011/0116710 A1* | 5/2011 | Garg | G06T 5/005 382/165 |
| 2012/0181452 A1* | 7/2012 | Trupke | G01N 21/6489 250/459.1 |
| 2013/0266893 A1* | 10/2013 | Gyoda | G03F 1/70 430/5 |
| 2015/0049936 A1* | 2/2015 | Tsunomori | G01N 21/6456 382/133 |
| 2015/0182120 A1* | 7/2015 | Sumi | A61B 5/0066 433/29 |
| 2017/0345615 A1* | 11/2017 | Zotta | G06T 5/003 |
| 2018/0109698 A1* | 4/2018 | Ramsay | A61B 8/0825 |
| 2018/0112173 A1* | 4/2018 | Wiles | G06T 7/0016 |
| 2018/0195973 A1* | 7/2018 | Yonekawa | E01C 23/01 |
| 2019/0080146 A1* | 3/2019 | Santamaria-Pang | G06T 7/0012 |
| 2019/0080165 A1* | 3/2019 | Takahashi | G06T 7/00 |
| 2019/0236778 A1* | 8/2019 | Saigo | G06K 9/00147 |
| 2020/0043159 A1* | 2/2020 | Watanabe | G06K 9/46 |

FOREIGN PATENT DOCUMENTS

| | | |
|---|---|---|
| CN | 109003248 A | 12/2018 |
| KR | 10-1653115 B1 | 9/2016 |

* cited by examiner

CHARACTERIZATION METHOD FOR FINE-GRAINED SEDIMENTARY ROCK LAMINAR TEXTURE

CROSS-REFERENCE TO RELATED APPLICATION

The present application is a continuation-in-part application of International Application No. PCT/CN2019/084171 filed on Apr. 25, 2019 which claims priority to Chinese Patent Application No. 201810813521.7 filed on Jul. 23, 2018. The disclosures of the aforementioned applications are hereby incorporated by reference in their entirety.

TECHNICAL FIELD

The present application belongs to the technical field of unconventional shale oil-gas exploration, and particularly relates to a characterization method for fine-grained sedimentary rock laminar texture.

BACKGROUND OF THE PRESENT INVENTION

In recent years, with the major breakthrough of shale gas in the United States, fine-grained sedimentary rock has gradually received high attention. In China, after a breakthrough from the gas well No. Wei-201 in Sichuan Province in 2014, this indicates that China has made new progress in the exploration and development of unconventional oil and gas resources. However, it can be found from a dozen shale gas wells (such as Well Niuye 1, Well Liangye 1, Well Liye 1, Well Fanye 1 and Well Boyeping 1) drilled in the past two years there was no obvious breakthrough has been made in the exploitation of shale oil and gas in lacustrine fine-grained sedimentary rock. This shows that there are still a series of problems need to be solved in the theoretical technologies of continental shale gas exploration and development in China. Particularly, the fracability of fine-grained sedimentary rock is one of important factors. The quantitative characterization of the laminar texture is also the basis for evaluating the fracability. Therefore, the research of studing characterization methods for fine-grained sedimentary rock laminar textures has great significance for the exploration and development of shale oil and gas in China to study fine-grained.

SUMMARY OF THE PRESENT INVENTION

In view of the problems such as the difficulty in quantitative characterization of a laminar texture in a prior fine-grained sedimentary rock oil-gas development process, the present application provides a characterization method capable of characterizing a fine-grained sedimentary rock laminar texture.

For this purpose, the present application provides a characterization method for a fine-grained sedimentary rock laminar texture, including the following specific steps:

S1: image preprocessing:
acquiring a microscopic image of a fine-grained sedimentary rock thin section, and daubing non-laminar feature in the microscopic image of the fine-grained sedimentary rock thin section;

S2: loading the image, and normalizing the image to a specified size, such as a specified pixel;

S3: performing mean filtering, dilation operation and binarization processing on the image successively;

S4: determining whether laminars are developed or not:
counting bright pixel points in each row of the image; setting a first threshold according to peaks, i.e., high values of the bright pixel points; and determining whether laminars are developed in the image according to the first threshold;

S5: determining the number of bright laminars and dark laminars:
setting a second threshold, finding the positions of troughs according to adjacent two peaks; if an elevation difference between a peak and an adjacent trough is greater than the second threshold, considering that there is a trough; and acquiring the accurate positions of peaks and troughs, i.e., effective peaks and effective troughs; wherein the number of effective peaks is the number of bright laminars, and the number of effective troughs is the number of dark laminars;

S6: determining the continuity of bright laminars and dark laminars:
in the bright laminars or the dark laminars, counting the number of corresponding break points by using the pixel points in each row of the image as a unit; obtaining a reciprocal of the average number of break points; and using the size of the reciprocal to characterize the strength of the continuity of bright laminars or the continuity of dark laminars; and, S7: according to the statistical and the calculation result, writing the number of bright laminars, the number of dark laminars, the average width of bright laminars, the average width of dark laminars, the average width of bright and dark laminars, the continuity of bright laminars, the continuity of dark laminar, the continuity of bright and dark laminars, the width variance of bright laminars, the width variance of dark laminars and the average width variance of bright and dark laminars into Excel.

Preferably, in S3, by the mean filtering, a mean value of neighboring pixel points is used to represent a target pixel point, thus target pixel points (i.e., local defects) are removed, and effective pixels are obtained; by the dilation operation, the effective pixels are expanded, and an overall defect after the mean filtering is eliminated; and, by the binarization processing, the gray values of pixel points on the image are set as 0 or 255, so that an obvious black-white image is presented.

Preferably, in S4, a waveform graph can be obtained by counting the bright pixel points in each row of the image; peaks of the image are acquired by a function [v1,l1] =attain_peak(y1,threshold1), where [v1,l1] represents a peak value, y1 is an accumulated value of transverse pixel points, and threshold1 is a peak threshold, i.e., a first threshold; if the v1 value exceeds the peak threshold, it is considered that there is a peak, and it is determined that there is a laminar; and, if the returned v1 value is null, there is no peak, and it is determined that there is no laminar.

Preferably, in S5, the positions of troughs are determined by a function [bright_stripe,dull_stripe,stripe_map]=cal_index(y1,[v1,l1],bw,threshold2), where bright_stripe represents a bright laminar, the dull_stripe represents a dark laminar, stripe_map represents a laminar simulated map, bw represents a binary image, the size of the laminar simulated map is obtained by the bw, and threshold2 is the second threshold; the positions of the troughs are obtained according to adjacent two peaks; if an elevation difference between a peak and an adjacent trough is greater than the threshold2, it is considered that there is a trough, so that the positions of peaks and troughs, i.e., effective peaks and effective troughs, can be accurately obtained, wherein the number of effective peaks is the number of bright laminars and the number of effective troughs is the number of dark laminars, so that the number of bright and dark laminars is determined.

Preferably, a method for calculating the bandwidth of bright laminars and dark laminars is set. For example, if a boundary value of bright and dark laminars is ⅖ or ½ of the peak or the like, the width of each bright laminar and the width of each dark laminar can be obtained.

Preferably, in S6, in accordance with the result of binarization processing, if the adjacent pixel points in each row of the image are the same in color, it is recorded as a break point.

Preferably, in S6, the process of determining the continuity of bright laminars is as follows: the number of dark break points among the pixel points in each row of each bright laminar is counted; an average number of break points (i.e., a first average number) is further obtained according to the total number of rows of each bright laminar; and an average number of dark break points (i.e., a second average number) of the image is calculated according to the number of bright laminars, where the reciprocal of the second average number is the continuity of bright laminars in the image.

Preferably, in S6, the process of determining the continuity of dark laminars is as follows: the number of bright break points among the pixel points in each row of each dark laminar is counted; an average number of break points (i.e., a third average number) is further obtained according to the total number of rows of each dark laminar; and an average number of bright break points (i.e., a fourth average number) of the image is calculated according to the number of dark laminars, where the reciprocal of the fourth average number is the continuity of dark laminars in the image.

Preferably, in S6, the continuity of bright laminars and the continuity of dark laminars are averaged to obtain the continuity of bright and dark laminars in the image.

Optionally, in S4, a waveform graph is obtained by counting the bright pixel points in each row of the image; the first threshold is selected, the peaks higher than the first threshold are selected as initial peaks, and it is determined that there are laminars; otherwise, it is determined that there is no laminar.

Optionally, the second threshold is set, and the positions of troughs are found by adjacent two initial peaks; if the elevation difference between an initial peak and a trough is greater than the second threshold, this trough is selected as an effective trough; and, if the elevation difference between an initial peak and a trough is less than or equal to the second threshold, this initial peak and the corresponding trough are removed, so that peaks after further screening, i.e., effective peaks, are obtained, and effective troughs are finally determined.

Optionally, the bandwidth of bright and dark laminars is set according to the effective peaks and the effective troughs; and the width of each bright laminar and the width of each dark laminar are obtained.

Optionally, a boundary value of bright and dark laminars is set as ⅖ of the peak, so that the width of each bright laminar and the width of each dark laminar are obtained.

Optionally, the process of determining the continuity of bright laminars is as follows: the number of dark break points among the pixel points in each row of each bright laminar is counted; an average number of break points is further obtained according to the total number of rows of each bright laminar; and an average number of dark break points of the image is calculated according to the number of bright laminars, where the reciprocal of the average number of dark break points is the continuity of bright laminars in the image;

the process of determining the continuity of dark laminars is as follows: the number of bright break points among the pixel points in each row of each dark laminar is counted; an average number of break points is further obtained according to the total number of rows of each dark laminar; and an average number of bright break points of the image is calculated according to the number of dark laminars, where the reciprocal of the average number of bright break points is the continuity of dark laminars in the image; and, the continuity of bright laminars and the continuity of dark laminars are averaged to obtain the continuity of bright and dark laminars in the image.

Compared with the prior art, the present application has the following beneficial effects.

(1) In the present application, the fine-grained sedimentary rock laminar texture is quantitatively characterized by an image analysis method, the process is convenient and fast, and the develop features of fine-grained sedimentary rock laminar can be accurately depicted. Thus, the requirement of symmetrically depicting the develop features of fine-grained sedimentary rock laminar is satisfied, the problems of high time consumption and low accuracy in the artificial statistics are fundamentally solved, and a technical support is provided for the exploration and development of shale oil and gas.

(2) In the present application, based on the relevant theories of the sedimentology, the respective characteristics of bright and dark laminars of fine-grained sedimentary rock and the comprehensive characteristics of bright and dark laminars are quantitatively depicted, respectively; and the difference in thickness between different laminars is quantified by using a mathematical variance as an index.

(3) In the present application, by counting the number of break points corresponding to the bright and dark laminars and then calculating the corresponding reciprocals to characterize the continuity of laminar, it accords with the meaning of the continuity in the sedimentology, and the reliable numerical basis is provided for evaluating the influences of the continuity of laminar on other factors (e.g., the brittleness, fracture toughness and fracability of the rock).

DETAILED DESCRIPTION OF THE PRESENT INVENTION

The present application will be specifically described below by exemplary implementations. However, it should be understood that an element, structure or feature in an implementation can also be beneficially incorporated into other implementations without further description.

It is to be noted that, for the fine-grained sedimentary rock mentioned in the present application, the research object in China is generally sedimentary rocks having a particle size less than or equal to 0.01 mm, while the research object in foreign countries is generally sedimentary rocks having a particle size less than or equal to 0.0039 mm. At least for these sedimentary rocks having such a particple size, the characterization method described in the present application is applicable.

Figure 1:
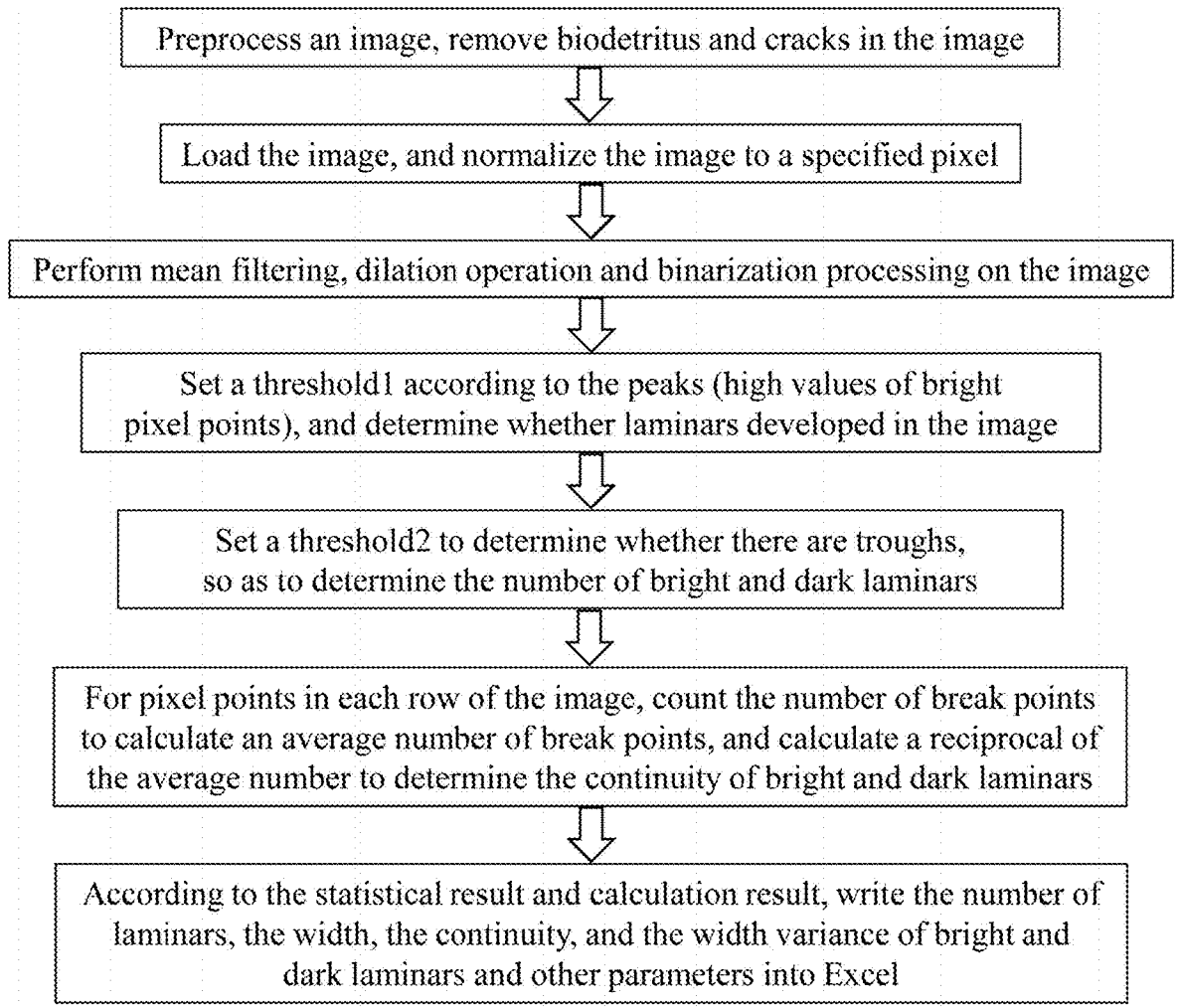
FIG. 1 is a flowchart of the characterization method for a fine-grained sedimentary rock laminar texture according to the present application.

With reference to FIG. 1, the present application discloses a characterization method for a fine-grained sedimentary rock laminar texture, including the following specific steps.

S1: image preprocessing:

A microscopic image of a fine-grained sedimentary rock thin section is acquired, and a non-laminar feature in the microscopic image of the fine-grained sedimentary rock thin section is daubed, wherein the non-stripe feature mainly includes biodetritus, crack or other features.

By daubing the non-laminar feature, the obtained information about the laminar can be more accurate.

S2: The image is loaded, and the image is normalized to a specified size, such as a specified or unified pixel.

Particularly when multiple different images are analyzed simultaneously, the finally obtained result may have higher comparability by normalizing these images to a unified or specified pixel size.

S3: Mean filtering, dilation operation and binarization processing are successively performed on the image; specifically:

By the mean filtering, a mean value of neighboring pixel points is used to represent a target pixel point, and the target pixel points (i.e., local defects) are removed to obtain effective pixels; by the dilation operation, the effective pixels are expanded, and an overall defect after the mean filtering is eliminated; and, by the binarization processing, the gray values of pixel points on the image are set as 0 or 255, so that an obvious black-white image is presented.

S4: Determining whether laminars are developed.

Bright pixel points of each row of the image are counted so that a waveform graph can be obtained; a first threshold is set according to peaks (i.e., high values of the bright pixel points); and, according to the first threshold, it is determined whether laminars are developed in the image.

S5: Determining the number of bright laminars and dark laminars:

A second threshold is set, the positions of troughs are found according to each adjacent two peaks; if an elevation difference between a peak and an adjacent trough is greater than the second threshold, it is considered that there is a trough, and the accurate positions of peaks and troughs, i.e., effective peaks and effective troughs, are acquired, wherein the number of effective peaks is the number of bright laminars and the number of effective troughs is the number of dark laminars.

S6: Determining the continuity of bright laminars and dark laminars:

In accordance with the result of binarization processing, if the adjacent pixel points in each row of the image are the same in color, it is recorded as a break point. In the bright laminars or dark laminars, the number of corresponding break points is counted by using the pixel points in each row of the image as a unit; a reciprocal of the average number of break points is calculated, and the strength of the continuity of bright laminars or the continuity of dark laminars is characterized by using the size of the reciprocal.

S7: The number of bright laminars, the number of dark laminars, the average width of bright laminars, the average width of dark laminars, the average width of bright and dark laminars, the continuity of bright laminars, the continuity of dark laminar, the continuity of bright and dark laminars, the width variance of bright laminars, the width variance of dark laminars and the average width variance of bright and dark laminars are written into Excel according to the statistical result and the calculation result.

In the method of the present application, based on fine-grained sedimentary rock thin section, the number of laminars, the width of laminars, the width difference between laminars and the continuity of laminars are quantitatively characterized by the image analysis method. Particularly, the width difference between laminars is characterized by a mathematical variance, and the continuity of laminars is characterized by counting the number of break points. Thus, the texture features of fine-grained sedimentary rock laminar can be accurately characterized. Moreover, compared with the prior art, the better effect is achieved, the requirement of symmetrically depicting the growth features of fine-grained sedimentary rock laminar is satisfied, and a technical support is provided for the exploration and development of shale oil and gas.

As a preferred design of the method, in S4, peaks of the image are acquired by a function [v1,l1]=attain_peak(y1, threshold1), where [v1,l1] represents a peak value, y1 is an accumulated value of transverse pixel points in the binarized image, and threshold1 is a peak threshold, i.e., the first threshold; if the v1 value exceeds the first threshold, it is considered that there is a peak, and it is determined that there is a laminar; and, if the returned v1 value is null, there is no peak, and it is determined that there is no laminar.

As a preferred design of the method, in S5, the positions of troughs are determined by a function [bright_stripe, dull_stripe,stripe_map]=cal_index(y1,[v1,l1],bw,threshold2), where bright_stripe represents a bright laminar, the dull_stripe represents a dark laminar, stripe_map represents a laminar simulated map, bw represents a binary image, the size of the laminar simulated map is obtained by the bw, and threshold2 is the second threshold; the position of the trough is obtained according to two adjacent peaks; if an elevation difference between a peak and an adjacent trough is greater than the threshold2, it is considered that there is a trough, so that the positions of peaks and troughs, i.e., effective peaks and effective troughs, can be accurately obtained, wherein the number of effective peaks is the number of bright laminars and the number of effective troughs is the number of dark laminars, so that the number of bright and dark laminars is determined.

It can be found from the above steps that, in the present application, after the first threshold is set, some initial peaks can be selected; and after the second threshold is set, effective peaks are further screened from the initial peaks, and effective troughs can also be determined.

In order to facilitate statistics and determine the average width of bright laminars, the average width of dark laminars, the average width of bright and dark laminars and the average width variance of bright and dark laminars, it is necessary to set the bandwidth of bright laminars and the bandwidth of dark laminars. In the process of setting the bandwidth of bright laminars and the bandwidth of dark laminars, since there are bright-dark transition zones between the bright laminars and the dark laminars, referring to FIG. 6, it is preferable that a boundary value of bright and dark laminars is set as ⅖ of the peak. However, other ratios can also be taken into consideration according to the gradation rule for bright and dark laminars under specific geological conditions. For example, ½, ⅗ or the like can be set.

After the bandwidth calculation method has been set, the width of each bright laminar and the width of each dark laminar can be obtained. The methods for calculating the average width and the average width variance belong to common mathematical knowledge and will not be repeated here.

As a preferred design of the method, in S6, the process of determining the continuity of bright laminars is as follows: the number of dark break points among the pixel points in each row of each bright laminar is counted; an average number of break points (i.e., a first average number) is further obtained according to the total number of rows of each bright laminar; and an average number of dark break points (i.e., a second average number) of the image is calculated according to the number of bright laminars, where the reciprocal of the second average number is the continuity of bright laminars of the image. The process of determining the continuity of dark laminars is as follows: the number of bright break points among the pixel points in each row of each dark laminar is counted; an average number of break points (i.e., a third average number) is further obtained according to the total number of rows of each dark laminar; and an average number of bright break points (i.e., a fourth average number) of the image is calculated according to the number of dark laminars, where the reciprocal of the fourth average number is the continuity of dark laminars of the image. The continuity of bright laminars and the continuity of dark laminars are averaged to obtain the continuity of bright and dark laminars of the image.

Generally, if there are more break points, the continuity of image laminars is lower; or otherwise, the continuity is higher. Additionally, in order to facilitate comparative analysis, the continuity can also be normalized. That is, for the fine-grained sedimentary rock having a continuity closer to 1, the continuity of laminars is higher; otherwise, if the continuity is closer to 0, the continuity of laminars is lower.

In order to describe the method more clearly, different embodiments will further be described as below.

Embodiment 1

The fine-grained sedimentary rock at 3296.44 m of Well NY1 in Dongying Sag of Jiyang Depression is used as a research object, and the laminar texture is characterized by the above method in the present application. With continued reference to FIG. 1, the specific steps are as follows.

Figure 2:
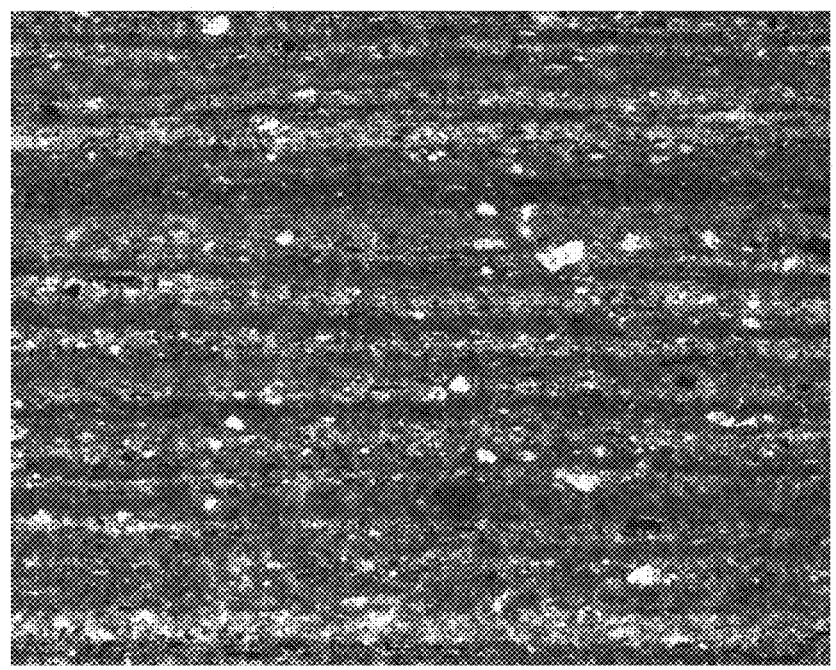
FIG. 2 is a microscopic image of a fine-grained sedimentary rock thin section before image processing according to Embodiment 1 of the present application.

S1: An image of the fine-grained sedimentary rock in the research region in this embodiment is selected. The microscopic image of the rock thin section before image processing refers to FIG. 2. Biodetritus and cracks in the microscopic image of the fine-grained sedimentary rock thin section are daubed by Photoshop to eliminate factors of the non-laminar features.

S2: The image is loaded and then normalized to a specified size. In this embodiment, the pixel selected for the specified size is 1944×2592, that is, the specified size is with a length of 2592 pixel points and a width of 1944 pixel points, so that uniform characterization parameter values can be obtained after processing.

For example, for fine-grained sedimentary rocks in different batches or from different locations, the same standard of 1944×2592 pixels is used, so that the obtained data can be based on the same pixel value and the obtained results have higher comparability.

S3: Mean filtering is performed on the image; a mean value of neighboring pixel points is used to represent a target pixel point, thus the target pixel point is removed, and an effective pixel is obtained; then, a dilation operation is performed and the effective pixel is expanded; and finally, binarization processing is performed, and the gray values of pixel points on the image are set as 0 or 255, so that an obvious black-white image is presented. The result of processing refers to FIG. 3.

S4: Bright pixel points of each row of the image are counted, a first threshold is set according to peaks (i.e., high values of the bright pixel points), and according to the first threshold, it is determined whether a laminar is developed in the image.

Figure 3:
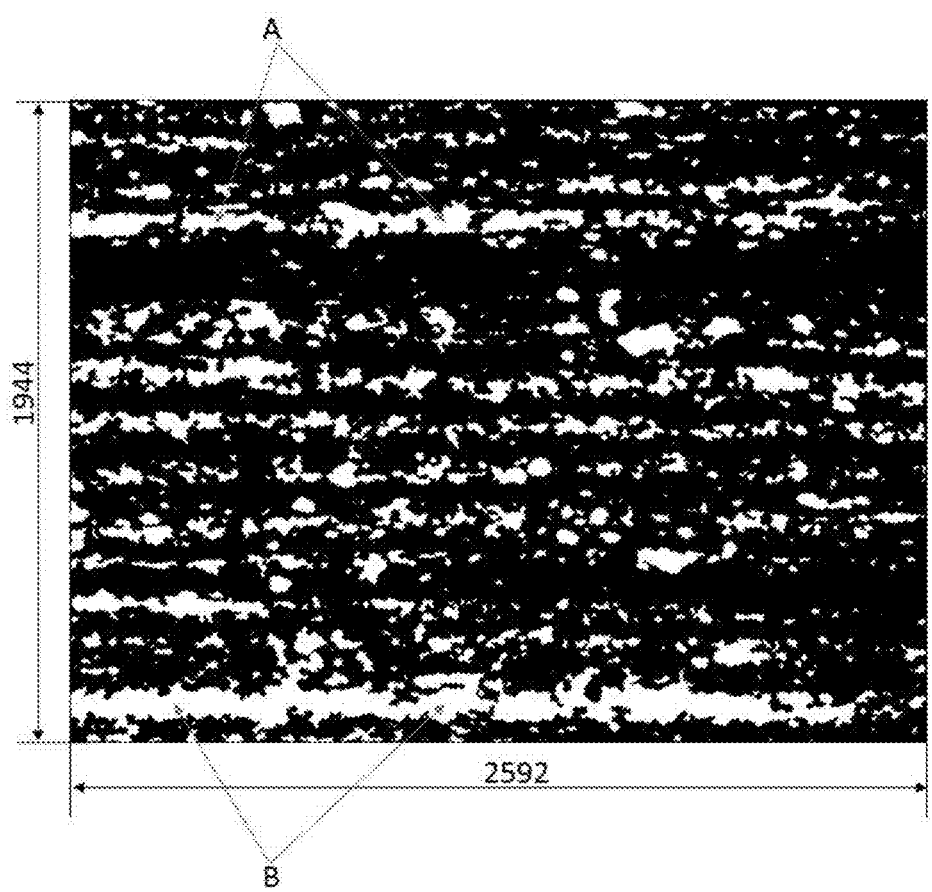
FIG. 3 is a diagram showing the result of mean filtering, dilation operation and binarization processing which are based on FIG. 2.
Figure 4:
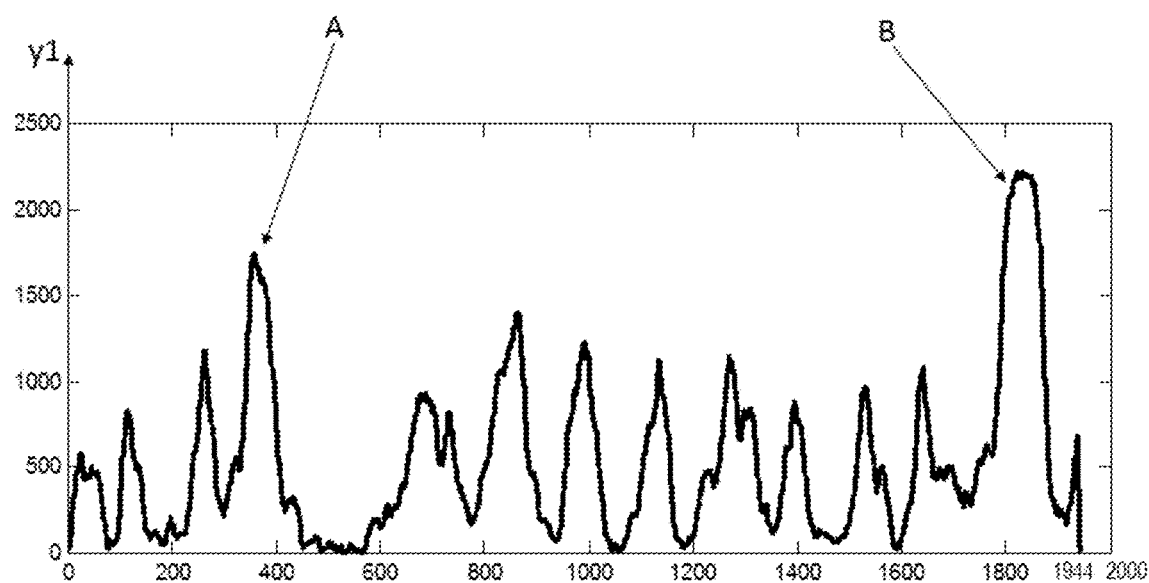
FIG. 4 is a waveform graph accumulated by bright pixel points in each row on FIG. 3.

Peaks of the image are acquired by a function $[v1,l1]$ =attain_peak(y1,threshold1), wherein, $[v1,l1]$ represents a peak value, y1 is an accumulated value of transverse pixel points in FIG. 3, the result of accumulation of y1 refers to FIG. 4, and threshold1 is a peak threshold, i.e., the first threshold. If the v1 value exceeds the peak threshold, it is considered that there is a peak, and it is determined that there is a laminar; and, if the returned v1 value is null, there is no peak, and it is determined that there is no laminar.

Specifically, referring to FIGS. 3 and 4, there are 2592 transverse pixel points and 1944 longitudinal pixel points in FIG. 3. The number of bright pixel points in each row (total 1944 rows) in FIG. 3 is counted. The 1944 longitudinal pixel points in FIG. 3 are used as horizontal coordinates in FIG. 4, and the counted number of bright pixel points is used as the vertical coordinate in FIG. 4, so that a waveform graph shown in FIG. 4 is obtained. For example, there are two larger bright pixel point regions at region A and region B in FIG. 3, where there are more bright pixel points; and this is correspondingly reflected in FIG. 4, and the peaks are higher. The first threshold is used for determining peaks preliminarily. The first threshold can be selected according to actual conditions or needs. For example, the selection of the first threshold can refer to the obtained waveform graph. Or, if it is expected that the obtained processing result is more detailed, the first threshold can be a smaller value; and, if it is expected that the obtained result is relatively rough, the first threshold can be larger. In this embodiment, the selection of the first threshold mainly refers to the formed waveform graph, and the first threshold is selected as 500. In FIG. 4, all peaks higher than 500 are selected as initial peaks, and it is determined that there are laminars; and, the ones less than 500 are determined as no laminars.

Initial peaks of the image can be obtained by calling the attain_peak function in the MATLAB and by using the function [v1,l1]=attain_peak(y1,threshold1), for example, so as to obtain coordinate values of each initial peak.

S5: A second threshold is set; the positions of troughs are found according to adjacent two peaks; if an elevation difference between a peak and an adjacent trough is greater than the second threshold, it is considered that there is a trough, and the accurate positions of peaks and troughs, i.e., effective peaks and effective troughs, are acquired, wherein the number of effective peaks is the number of bright laminars and the number of effective troughs is the number of dark laminars.

The position of a trough is determined by a function [bright_stripe,dull_stripe,stripe_map]=cal_index(y1,[v1,l1], bw,threshold2), where bright_stripe represents a bright laminar, the dull_stripe represents a dark laminar, stripe_map represents a laminar simulated map, bw represents a binary image, the size of the laminar simulated map is obtained by the bw, and threshold2 is the second threshold. The positions of the troughs are obtained according to each adjacent two peaks. If an elevation difference between a peak and an adjacent trough is greater than the threshold2, it is considered that there is a trough, so that the positions of peaks and troughs can be accurately obtained. At this time, the obtained peaks are effective peaks, and the obtained troughs are effective troughs. The number of effective peaks is the number of bright laminars, and the number of effective troughs is the number of dark laminars, so that the number of bright and dark laminars is determined. The result of the determined bright and dark laminars refers to FIG. 5. The bandwidth of dark laminars and the bandwidth of bright laminars are set according to the peaks and troughs. In the bandwidth setting process, referring to FIG. 6, a boundary value of bright and dark laminars is set as ⅔ of the peak in this embodiment, so that the average width of bright laminars, the average width of dark laminars, the average width of bright and dark laminars and the average width variance of bright and dark laminars are determined. The simulated laminars of the rock thin section refer to FIG. 7.

Specifically, after the second threshold is set, the positions of troughs are found by adjacent two initial peaks. If the elevation difference between an initial peak and a trough is greater than the second threshold, this trough is selected as an effective trough; and, if the elevation difference between an initial peak and a trough is less than or equal to the second threshold, this initial peak and the corresponding trough are removed, so that peaks after further screening (i.e., effective peaks) are obtained, and effective troughs can be finally determined.

Figure 5:
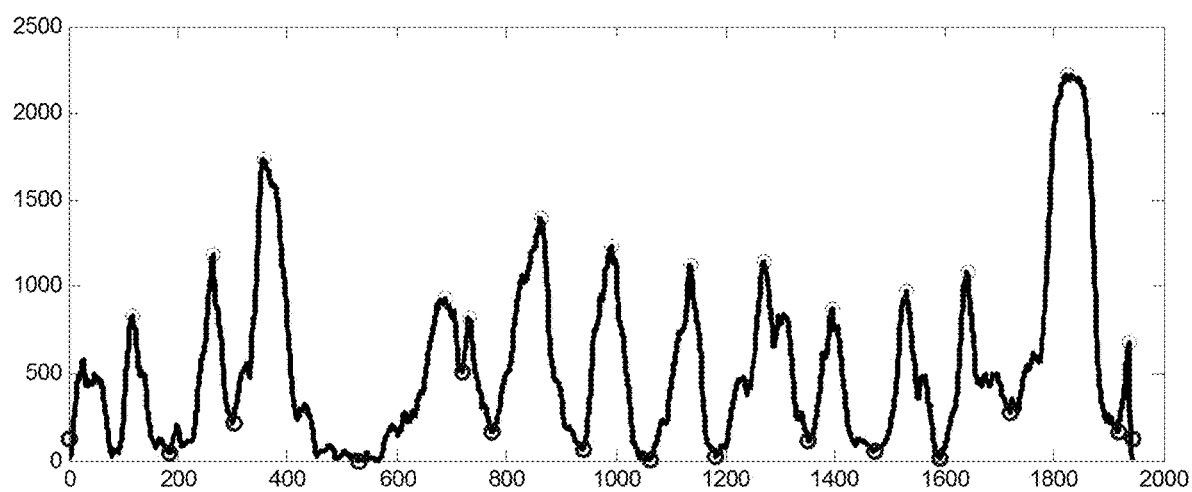
FIG. 5 is a schematic diagram of determining laminars by the first threshold and the second threshold in Embodiment 1.

The second threshold is used for determining troughs and further screening the initial peaks to eventually obtain effective peaks and effective troughs. The second threshold can be appropriately adjusted according to the laminar growth condition of the specific thin section. The second threshold is commonly between 200 and 300. For example, the second threshold can be, but not limited to, 200, 220, 240, 250, 260, 280, 300, etc. In this embodiment, the second threshold is selected as 300, the number of the obtained effective peaks is the number of bright laminars, and the number of the obtained effective troughs is the number of dark laminars. As shown in FIG. 5, 14 effective peaks and 15 effective troughs are obtained.

The positions of troughs can be determined by calling the cal_index function in the MATLAB software and by using the function [bright_stripe,dull_stripe,stripe_map]=cal_index(y1,[v1,l1],bw,threshold2). Then, the effective peaks and effective troughs are further calculated.

Figure 6:
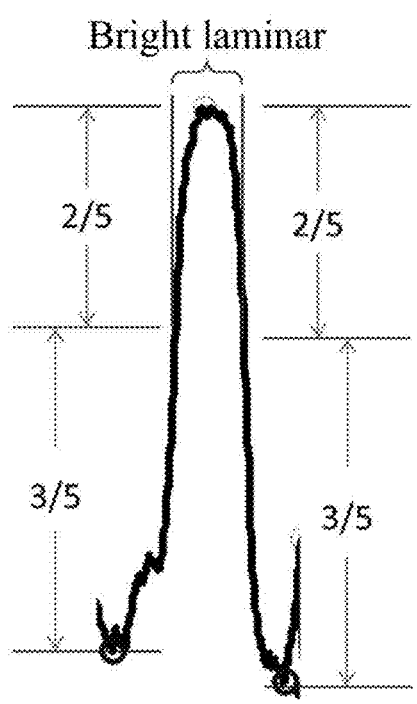
FIG. 6 is a diagram of a method for determining the laminar bandwidth in Embodiment 1.
Figure 7:
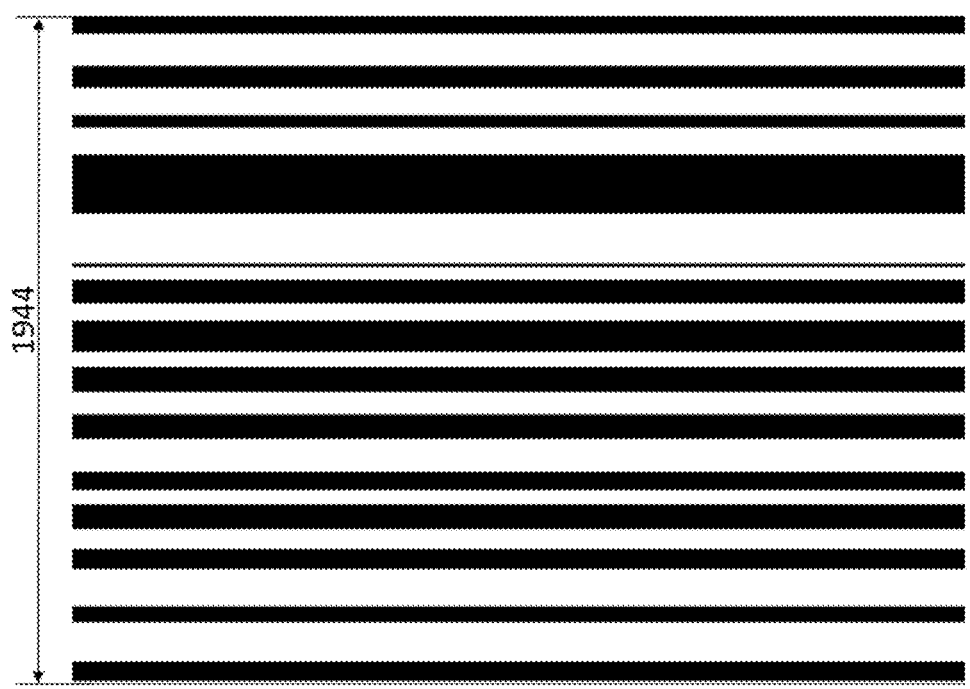
FIG. 7 is a simulated map of laminars in the image in Embodiment 1.

The bandwidth of bright and dark laminars can be set according to the effective peaks and the effective troughs. By taking the point B in FIG. 5 as an object, as shown in FIG. 6, when the boundary value of bright and dark laminars is set as ⅔ of the peak, the bright laminar correspondingly accounts for ⅖, and the dark laminars correspondingly account for ⅗, so that the width of each bright laminar and the width of each dark laminar can be obtained. The width corresponds to the number of pixel points, so that the simulated laminar map of the rock thin section shown in FIG. 7 is obtained. The total width of the bright laminars and the dark laminars is 1944 pixel points (it is apparent that there are more pixel points occupied if the width is larger), which correspond to the horizontal coordinates in FIG. 5. Moreover, FIG. 7 is the same as FIG. 3 in size. The average width of bright laminars, the average width of dark laminars, the average width of bright and dark laminars and the average width variance of bright and dark laminars can be further determined by the width of each bright laminar and the width of each dark laminar.

S6: In accordance with the result of binarization, if the adjacent pixel points in each row of the image are the same in color, it is recorded as a break point, referring to FIG. 8. The number of dark break points among the pixel points in each row of each bright laminar is counted; an average number of break points is further obtained according to the total number of rows of each bright laminar; and an average number of dark break points of the image is calculated according to the number of bright laminars, where the reciprocal of the average number of dark break points of the bright laminars in the image is the continuity of bright laminars in the image. The number of bright break points among the pixel points in each row of each dark laminar is counted; an average number of break points is further obtained according to the total number of rows of each dark laminar; and an average number of bright break points of the image is calculated according to the number of dark laminars, where the reciprocal of the average number of bright break points of the dark laminars in the image is the continuity of dark laminars in the image. The continuity of bright laminars and the continuity of dark laminars are averaged to obtain the continuity of bright and dark laminars in the image.

Specifically, it can be seen from the simulated laminar map shown in FIG. 7 that, in this embodiment, there are 14 bright laminars and 15 dark laminars. Thus, FIG. 3 can be longitudinally divided into 14 bright laminar regions and 15 dark laminar regions. Correspondingly, in FIG. 3, there are multiple pixel rows in each laminar region, and all the laminar regions correspond to 1944 pixel rows. In FIG. 3, for the dark laminar regions, the number of bright break points in each row of each dark laminar region is counted; and, for the bright laminar regions, the number of dark break points in each row of each bright laminar region is counted.

Figure 8:
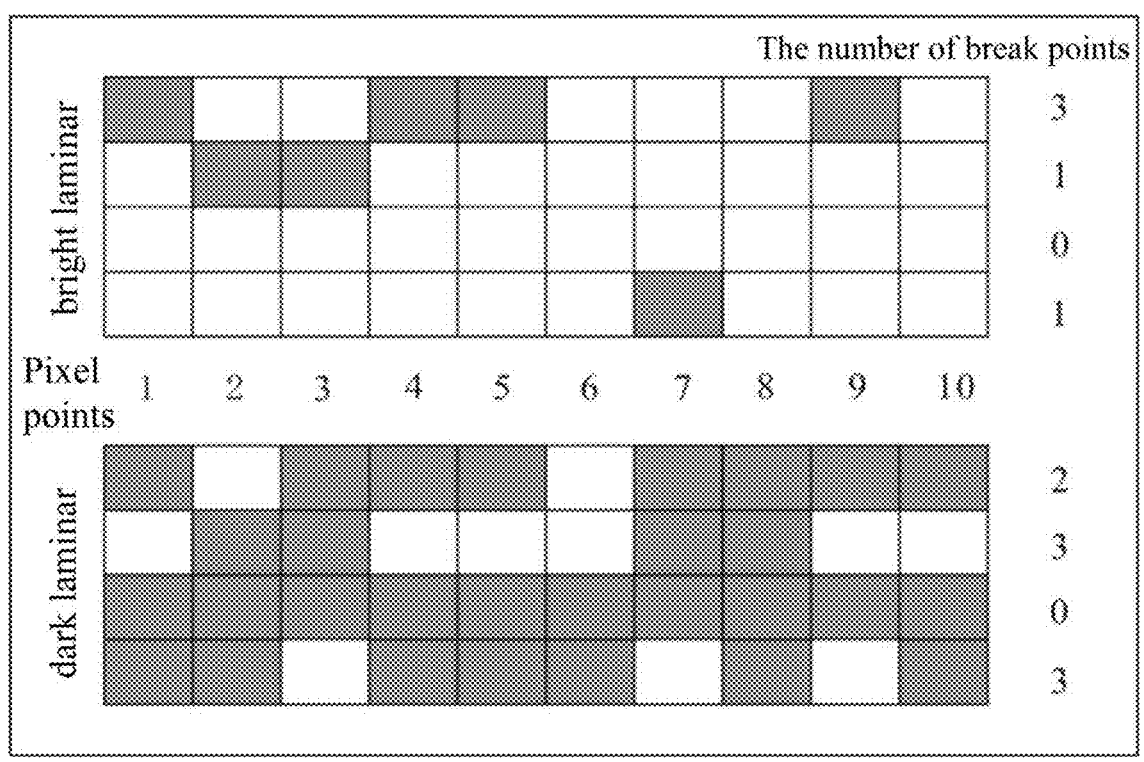
FIG. 8 is a diagram showing an example of calculating the continuity of laminars in Embodiment 1.

The method for counting the number of break points will be described by taking FIG. 8 as example. It is to be noted that an example of counting 10 pixel points in each row is shown in FIG. 8; however, in the present application, there are actually 2592 pixel points in each row. FIG. 8 also exemplarily shows one bright laminar region and one dark laminar region. In FIG. 8, for each row of the bright laminar region, adjacent dark pixels are recorded as one dark break point, so the number of dark break points in the rows of the bright laminar region in this example is 3, 1, 0 and 1, respectively; and, for each row of the dark laminar region, in a similar way, adjacent bright pixels are recorded as a bright break point, so the number of bright peak points in the rows in this example is 2, 3, 0 and 3, respectively. Using this method, after the number of dark break points in each row of each of the 14 bright laminar regions is counted, an average number of break points of the bright laminars can be obtained by averaging, and the reciprocal of the average number is used as the continuity of bright laminars. Similarly, the average number of break points of the dark laminars and the continuity of bright laminars can be obtained. The continuity of bright laminars and the continuity of dark laminars are averaged to obtain the continuity of bright and dark laminars.

S7: The number of bright laminars, the number of dark laminars, the average width of bright laminars, the average width of dark laminars, the average width of bright and dark laminars, the continuity of bright laminars, the continuity of dark laminar, the continuity of bright and dark laminars, the width variance of bright laminars, the width variance of dark laminars, and the average width variance of bright and dark laminars are written into Excel according to the statistical result and the result of calculation. The result of the characterization refers to Table 1.

TABLE 1

| Output type | Value |
| --- | --- |
| The number of bright laminars | 14 |
| The continuity of bright laminars | 0.2877 |
| The average width of bright laminars | 0.0508 mm |
| The width variance of bright laminars | 0.1205 |
| The average continuity of bright and dark laminars | 0.3360 |
| The average width of bright and dark laminars | 0.0467 mm |
| The number of dark laminars | 15 |
| The continuity of dark laminars | 0.3844 |
| The average width of dark laminars | 0.0425 mm |
| The width variance of dark laminars | 0.1380 |
| The average continuity of bright and dark laminars | 0.1292 |

It is to be noted that the unit of the width given in Table is mm, instead of the number of pixel points. This is because the actual length of the thin section image corresponding to 1944*2592 pixels in this embodiment is 1350 μm*1800 μm, after the corresponding pixel points are obtained, the pixel points are converted into an actual length in unit of mm.

Embodiment 2

The fine-grained sedimentary rock at 3,451.85 m of Well NY1 in Dongying Sag of Jiyang Depression is used as a research object, and the laminar texture is characterized by the above method in the present application. With continued reference to FIG. 1, the specific steps are as follows.

Figure 9:
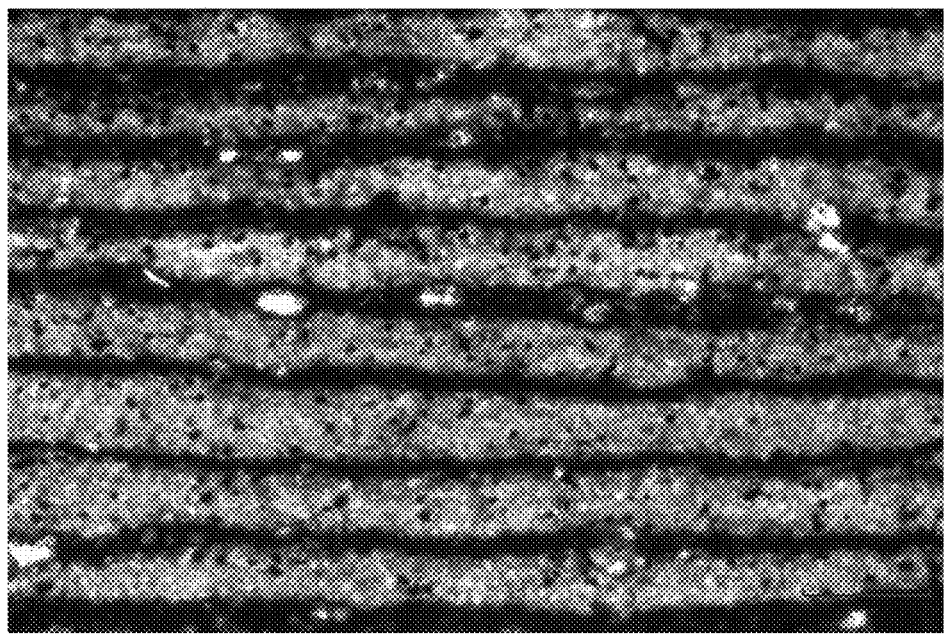
FIG. 9 is a microscopic image of a fine-grained sedimentary rock thin section before image processing according to Embodiment 2 of the present application.

S1: An image of the fine-grained sedimentary rock in the research region in this embodiment is selected. The microscopic image of the rock thin section before image processing refers to FIG. 9. Biodetritus and cracks in the microscopic image of the fine-grained sedimentary rock thin section are smeared by Photoshop to eliminate factors of the non-laminar features.

S2: The image is loaded and then normalized to a specified size. In this embodiment, the pixel selected for the specified size is 1944×2592, that is, the specified size is with a length of 2592 pixel points and a width of 1944 pixel points, so that uniform characterization parameter values can be obtained after processing. Since the same pixel is used in both Embodiments 1 and 2, a higher comparability is realized for the two embodiments.

Figure 10:
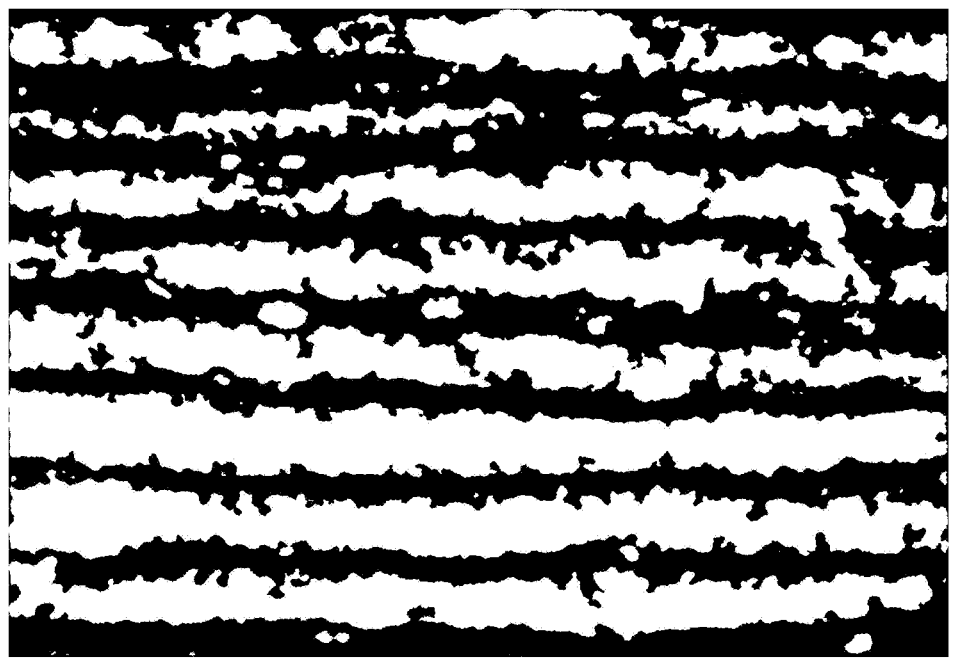
FIG. 10 is a diagram showing the result of mean filtering, dilation operation and binarization processing performed on FIG. 9.

S3: Mean filtering is performed on the image; a mean value of neighboring pixel points is used to represent a target pixel point, and the target pixel points (i.e., local defects) are removed, and effective pixels are obtained; then, a dilation operation is performed and the effective pixels are expanded, to eliminate the overall defect in the image after the mean filtering; and finally, binarization processing is performed, and the gray values of pixel points on the image are set as 0 or 255, so that an obvious black-white image is presented. The result of processing refers to FIG. 10.

S4: Peaks of the image are acquired by a function [v1, l1]=attain_peak(y1,threshold1), where [v1,l1] represents a peak value, y1 is an accumulated value of transverse pixel points, and threshold1 is a peak threshold, i.e., a first threshold. If the v1 value exceeds the peak threshold, it is considered that there is a peak, and it is determined that there is a laminar; and, if the v1 value is null, there is no peak, and it is determined that there is no laminar.

Figure 11:
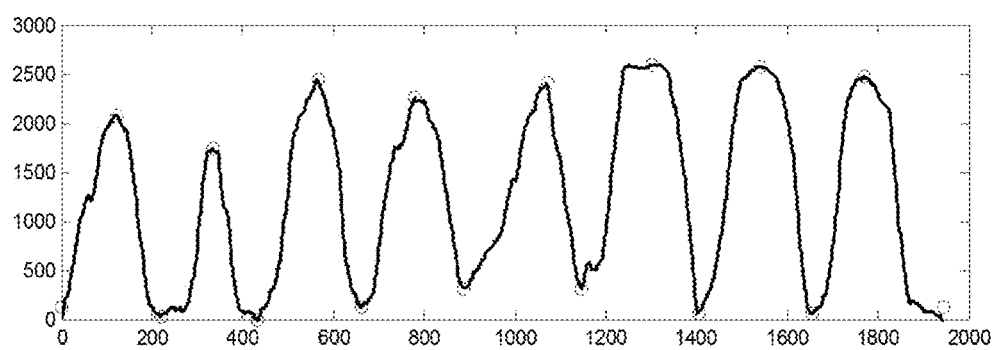
FIG. 11 is a schematic diagram of determining laminars by the first threshold and the second threshold in Embodiment 2; and, FIG. 12 is a simulated map of laminars in the image in Embodiment 2.
Figure 12:
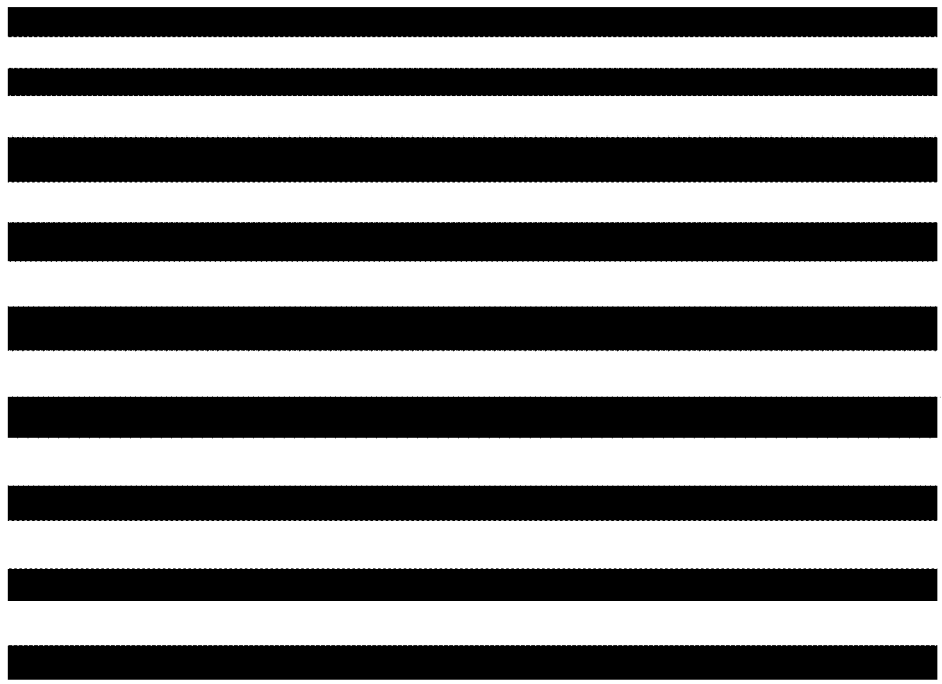

S5: The position of a trough is determined by a function [bright_stripe,dull_stripe,stripe_map]=cal_index(y1,[v1,l1], bw,threshold2), where bright_stripe represents a bright laminar, the dull_stripe represents a dark laminar, stripe_map represents a laminar simulated map, bw represents a binary image, the size of the simulated map is obtained by the bw, and threshold2 is a second threshold. The positions of the troughs are obtained according to adjacent two peaks. If an elevation difference between a peak and an adjacent trough is greater than the threshold2, it is considered that there is a trough, so that the positions of peaks and troughs can be accurately obtained, wherein the number of effective peaks is the number of bright laminars and the number of effective troughs is the number of dark laminars, so that the number of bright and dark laminars is determined. The result of the determined bright and dark laminars refers to FIG. 11. The simulated laminars of the rock thin section refer to FIG. 12. The bandwidth of dark laminars and the bandwidth of bright laminars are set according to the peaks and troughs. In the bandwidth setting process, referring to FIG. 6, the boundary value of bright and dark laminars is set as ⅖ of the peak, so that the average width of bright laminars, the average width of dark laminars, the average width of bright and dark laminars and the average width variance of bright and dark laminars are determined.

S6: In accordance with the result of binarization, if the adjacent pixel points in each row of the image are the same in color, it is recorded as a break point. The number of dark break points among the pixel points in each row of each bright laminar is counted; an average number of break points is further obtained according to the total number of rows of each bright laminar; and finally an average number of dark break points of the image is calculated according to the number of bright laminars, where the reciprocal of the average number of dark break points of the bright laminars in the image is the continuity of bright laminars in the image. The number of bright break points among the pixel points in each row of each dark laminar is counted; an average number of break points is further obtained according to the total number of rows of each dark laminar; and finally an average number of bright break points of the image is calculated according to the number of dark laminars, where the reciprocal of the average number of bright break points of the dark laminars in the image is the continuity of dark laminars in the image. The continuity of bright laminars and the continuity of dark laminars are averaged to obtain the continuity of bright and dark laminars in the image.

S7: The number of bright laminars, the number of dark laminars, the average width of bright laminars, the average width of dark laminars, the average width of bright and dark laminars, the continuity of bright laminars, the continuity of dark laminar, the continuity of bright and dark laminars, the width variance of bright laminars, the width variance of dark laminars; and the average width variance of bright and dark laminars are written into Excel according to the statistical result and the result of calculation. The result of the characterization refers to Table 2.

TABLE 2

| Output type | Value |
|---|---|
| The number of bright laminars | 8 |
| The continuity of bright laminars | 0.8631 |
| The average width of bright laminars | 0.0864 mm |
| The width variance of bright laminars | 0.0459 |
| The average continuity of bright and dark laminars | 0.9048 |
| The average width of bright and dark laminars | 0.0798 mm |
| The number of dark laminars | 9 |
| The continuity of dark laminars | 0.9464 |
| The average width of dark laminars | 0.0731 mm |
| The width variance of dark laminars | 0.0569 |
| The average width variance of bright and dark laminars | 0.0514 |

The processing steps and principles of Embodiment 2 are basically the same as those of Embodiment 1, wherein more detailed description is given in Embodiment 1 for easy understanding, and the related items will not be repeated in Embodiment 2.

Additionally, the width data given in Table 2 is the same as that in Table in principle, and the actual length of the corresponding thin section image is also 1350 μm*1800 μm.

It can be found from the above embodiments that, the characterization method in the present invention can use MATLAB software programming as method, and the image analysis method is adapted to quantitatively characterize the number of laminars, the width of laminars (i.e., the thickness of laminars), the width difference between laminars and the continuity of laminars of the fine-grained sedimentary rock. Particularly, the width difference between laminars is represented by a mathematical variance, and the continuity of laminars is characterized by counting the number of break points. Thus, the develop features of fine-grained sedimentary rock laminars can be symmetrically depicted, the fracability and development potential of the fine-grained sedimentary rock can be further accurately evaluated, and effective pressure operation modes and materials can be selected, so that a technical support is provided for the exploration and development of shale oil and gas in China.

The foregoing embodiments are merely for illustratively describing the present application, rather than limiting the protection scope of the present application. Various simple variations and modifications made by those skilled in the art without departing from the scope of the technical solutions of the present application shall fall into the patent scope of the present application.

What is claimed is:

1. A characterization method for a fine-grained sedimentary rock laminar texture, wherein, including the following specific steps:
S1: image preprocessing comprising the operations of:
acquiring a microscopic image of a fine-grained sedimentary rock thin section, and daubing non-laminar features in the microscopic image of the fine-grained sedimentary rock thin section;
S2: loading the microscopic image, and normalizing the microscopic image to a specified size;
S3: performing mean filtering, dilation operation and binarization processing on the microscopic image successively;
S4: determining whether laminars are developed through the operations of:
counting bright pixel points in each row of the image; setting a first threshold according to peaks, corresponding to high values of the bright pixel points; and determining, according to the first threshold, whether laminars are developed in the image;
S5: determining a number of bright laminars and dark laminars through the operations of:
setting a second threshold, finding the positions of troughs according to adjacent two peaks; wherein if an elevation difference between a peak and an adjacent trough is greater than the second threshold, determining that there is a trough; and acquiring accurate positions of peaks and troughs, corresponding to effective peaks and effective troughs, wherein the number of effective peaks is the number of bright laminars and the number of effective troughs is the number of dark laminars;
S6: determining a continuity of bright laminars and dark laminars through the operations of:
in the bright laminars or the dark laminars, counting a number of corresponding break points by using the bright pixel points in each row of the microscopic image as a unit; obtaining a reciprocal of an average number of break points; and using a size of the reciprocal to characterize a strength of the continuity of bright laminars or the continuity of dark laminars; and,
S7: according to the statistical result and the calculation result, writing the number of bright laminars, the number of dark laminars, the average width of bright laminars, the average width of dark laminars, the average width of bright and dark laminars, the continuity of bright laminars, the continuity of dark laminar, the continuity of bright and dark laminars, the width variance of bright laminars, the width variance of dark laminars, and the average width variance of bright and dark laminars into an Excel file.

2. The characterization method according to claim 1, wherein, in S3, by the mean filtering, a mean value of neighboring pixel points is used to represent a target pixel point, thus target pixel points are removed, and effective pixels are obtained; by the dilation operation, the effective pixels are expanded; and, by the binarization processing, gray values of pixel points on the image are set as 0 or 255, so that an obvious black-white image is presented.

3. The characterization method according to claim 2, wherein, in S4, peaks of the image are acquired by a function "[v1,l1]"=attain_peak("y1",threshold1), where [v1,l1] represents a peak value, y1 is an accumulated value of transverse pixel points, and threshold1 is a peak threshold, corresponding to a first threshold; wherein if the "v1" value exceeds the peak threshold, it is considered that there is a peak, and it is determined that there is a laminar; and, if the returned "v1" value is null, there is no peak, and it is determined that there is no laminar.

4. The characterization method according to claim 3, wherein, in S5, the positions of troughs are determined by a function [bright_stripe,dull_stripe,stripe_map]=cal_index (y1,[v1,l1],bw,threshold2), where "bright_stripe" represents a bright laminar, "dull_stripe" represents a dark laminar, "stripe_map" represents a laminar simulated map, "bw" represents a binary image, the size of the laminar simulated map is obtained by the "bw", and "threshold2" is the second threshold; the positions of the troughs are obtained according to adjacent two peaks; wherein if an elevation difference between a peak and an adjacent trough is greater than the "threshold2", it is determined that there is a trough, so that the positions of peaks and troughs, i.e., effective peaks and effective troughs, are obtained, wherein the number of effective peaks is the number of bright laminars and the number of effective troughs is the number of dark laminars, such that the number of bright and dark laminars is determined.

5. The characterization method according to claim 4, wherein, in S6, in accordance with the result of binarization processing, if the adjacent pixel points in each row of the image are the same in color, it is recorded as a break point.

6. The characterization method according to claim 5, wherein, in S6, the process of determining the continuity of bright laminars includes the operations of: the number of dark break points among the pixel points in each row of each bright laminar is counted; an average number of break points is further obtained according to the total number of rows of each bright laminar; and an average number of dark break points of the image is calculated according to the number of bright laminars, where the reciprocal of the average number of dark break points is the continuity of bright laminars in the image.

7. The characterization method according to claim 6, wherein, in S6, the process of determining the continuity of dark laminars includes the operations of: the number of bright break points among the pixel points in each row of each dark laminar is counted; an average number of break points is further obtained according to the total number of rows of each dark laminar; and an average number of bright break points of the image is calculated according to the number of dark laminars, where the reciprocal of the average number of bright break points is the continuity of dark laminars in the image.

8. The characterization method according to claim 7, wherein, in S6, the continuity of bright laminars and the continuity of dark laminars are averaged to obtain the continuity of bright and dark laminars in the image.

* * * * *